US009872765B2

(12) United States Patent
Zeng et al.

(10) Patent No.: US 9,872,765 B2
(45) Date of Patent: Jan. 23, 2018

(54) MITRAL VALVE ASSEMBLY

(71) Applicant: Horizon Scientific Corp., Irvine, CA (US)

(72) Inventors: Min Frank Zeng, Irvine, CA (US); Pham Lo, Irvine, CA (US)

(73) Assignee: Venus Medtech (Hangzhou) Inc (CN)

( * ) Notice: Subject to any disclaimer, the term of this patent is extended or adjusted under 35 U.S.C. 154(b) by 3 days.

(21) Appl. No.: 14/880,836

(22) Filed: Oct. 12, 2015

(65) Prior Publication Data
US 2017/0100240 A1 Apr. 13, 2017

(51) Int. Cl.
*A61F 2/24* (2006.01)
*A61F 2/915* (2013.01)

(52) U.S. Cl.
CPC .............. *A61F 2/2418* (2013.01); *A61F 2/24* (2013.01); *A61F 2/2412* (2013.01); *A61F 2/2433* (2013.01); *A61F 2/2436* (2013.01); *A61F 2/915* (2013.01); *A61F 2210/0014* (2013.01); *A61F 2210/0071* (2013.01); *A61F 2220/0075* (2013.01); *A61F 2230/0006* (2013.01); *A61F 2230/0021* (2013.01); *A61F 2230/0052* (2013.01); *A61F 2230/0071* (2013.01); *A61F 2250/0039* (2013.01); *A61F 2250/0067* (2013.01)

(58) Field of Classification Search
CPC ...... A61F 2/24–2/2424; A61F 2/2442–2/2448; A61F 2230/0071; A61F 2230/0076; A61F 2250/0039
See application file for complete search history.

(56) References Cited

U.S. PATENT DOCUMENTS

| 7,291,168 | B2 | 11/2007 | Macoviak et al. | |
|---|---|---|---|---|
| 7,611,534 | B2 | 11/2009 | Kapadia et al. | |
| 8,992,605 | B2 | 3/2015 | Zakai et al. | |
| 9,173,737 | B2 | 11/2015 | Hill et al. | |
| 9,387,072 | B2 | 7/2016 | Braido et al. | |
| 9,468,525 | B2 | 10/2016 | Kovalsky | |
| 9,603,705 | B2 | 3/2017 | Alkhatib | |
| 2006/0058871 | A1* | 3/2006 | Zakay ............... | A61B 17/00234 623/2.18 |
| 2007/0288087 | A1* | 12/2007 | Fearnot ................. | A61F 2/2418 623/1.24 |
| 2010/0217382 | A1* | 8/2010 | Chau ..................... | A61F 2/2418 623/1.26 |
| 2010/0280606 | A1* | 11/2010 | Naor ..................... | A61F 2/2418 623/2.18 |

(Continued)

OTHER PUBLICATIONS

PCT Search Report and Written Opinion dated Dec. 9, 2016 for PCT/US2016/055077.

*Primary Examiner* — Yashita Sharma
*Assistant Examiner* — Rebecca Preston

(57) ABSTRACT

A heart valve assembly has a frame having an anchoring section defined by a plurality of rows of cells, with each cell defined by a plurality of struts that encircle each cell, and a pair of legs extending from the anchoring section. The assembly also includes a leaflet assembly that has a plurality of leaflets that are stitched to the legs. The heart valve assembly is delivered to the location of a native mitral annulus, and the anchoring section is deployed inside the left atrium such that the anchoring section is completely retained in the left atrium, and the legs and leaflets extend through the native mitral annulus.

7 Claims, 7 Drawing Sheets

(56) References Cited

U.S. PATENT DOCUMENTS

| | | |
|---|---|---|
| 2011/0112632 A1 | 5/2011 | Chau et al. |
| 2014/0031928 A1 | 1/2014 | Murphy et al. |
| 2014/0222142 A1 | 8/2014 | Kovalsky et al. |
| 2015/0196390 A1 | 7/2015 | Ma et al. |
| 2016/0074164 A1* | 3/2016 | Naor .................... A61F 2/2418 623/2.11 |
| 2016/0089238 A1 | 3/2016 | Centola et al. |

* cited by examiner

MITRAL VALVE ASSEMBLY

BACKGROUND OF THE INVENTION

1. Field of the Invention

The present invention is directed to methods, systems, and apparatus for transcatheter placement of a mitral valve to restore mitral valve function in a patient.

2. Description of the Prior Art

Prosthetic heart valves have been used for many years to treat cardiac valvular disorders. The native heart valves (such as the aortic, pulmonary, and mitral valves) serve critical functions in assuring the forward flow of an adequate supply of blood through the cardiovascular system. These heart valves can be rendered less effective by congenital, inflammatory, or infectious conditions. Such conditions can eventually lead to serious cardiovascular compromise or death. For many years the definitive treatment for such disorders was the surgical repair or replacement of the valve during open heart surgery, but such surgeries are traumatic and prone to complication.

More recently a transvascular technique has been developed for introducing and implanting a prosthetic heart valve using a flexible catheter in a manner that is less invasive than open heart surgery. In this technique, a prosthetic valve is mounted in a crimped state on the end portion of a flexible catheter and advanced through a blood vessel of the patient until the valve reaches the implantation site. The valve at the catheter tip is then expanded to its functional size at the site of the defective native valve, such as by inflating a balloon on which the valve is mounted. Alternatively, the valve can have a resilient, self-expanding stent or frame that expands the valve to its functional size when it is advanced from a delivery sheath at the distal end of the catheter.

Unlike the aortic valve, however, the mitral valve annulus does not provide a good landmark for positioning a replacement mitral valve. In patients needing a replacement aortic valve, the height and width of the aortic annulus are generally increased in the presence of degenerative disease associated with calcium formation. These changes in tissue make it easier to properly secure a replacement aortic valve in place due to the reduced cross-sectional area of the aortic annulus. The degenerative changes typically found in aortic valves are not, however, present in mitral valves experiencing regurgitation, and a mitral valve annulus is therefore generally thinner than the annulus of a diseased aortic valve. The thinner mitral valve annulus makes it relatively more difficult to properly seat a replacement mitral valve in the native mitral valve annulus. The general anatomy of the mitral valve annulus also makes it more difficult to properly anchor a replacement mitral valve in place. The mitral valve annulus provides for a smoother transition from the left atrium to the left ventricle than the transition that the aortic valve annulus provides from the aorta to the left ventricle. The aortic annulus is anatomically more pronounced, providing a larger "bump" to which a replacement aortic valve can more easily be secured in place.

Thus, the larger mitral valve annulus makes it difficult to securely implant current percutaneously delivered valves in the native mitral position. Some attempts have been made to deliver and implant a one-piece replacement mitral valve by clamping on the annulus, or by hooking on the chordae and by expanding the implant frame to achieve a tight fit in the annulus. These methods will more or less alter the anatomy of the patient and affect the function of the aortic valve and the blood flow.

As a result, there remains a need for a replacement mitral valve that can be securely implanted at the native mitral position through percutaneous delivery, without distorting the patient's anatomy.

SUMMARY OF THE DISCLOSURE

The present invention provides a mitral valve assembly and associated delivery system that allows percutaneous transcatheter placement of a biological valve within a self-expanding stent at the native mitral position for a patient.

The present invention provides a heart valve assembly having a frame comprising an anchoring section defined by a plurality of rows of cells, with each cell defined by a plurality of struts that encircle each cell, and a pair of legs extending from the anchoring section. The assembly also includes a leaflet assembly that has a plurality of leaflets that are stitched to the legs. The anchoring section has a configuration that is similar to the configuration of a left atrium.

The present invention also provides a method for securing the heart valve assembly in the mitral position of a human heart. The heart valve assembly is delivered to the location of a native mitral annulus, and the anchoring section is deployed inside the left atrium such that the anchoring section is completely retained in the left atrium, and the legs and leaflets extend through the native mitral annulus.

DETAILED DESCRIPTION OF THE PREFERRED EMBODIMENTS

Figure 1:
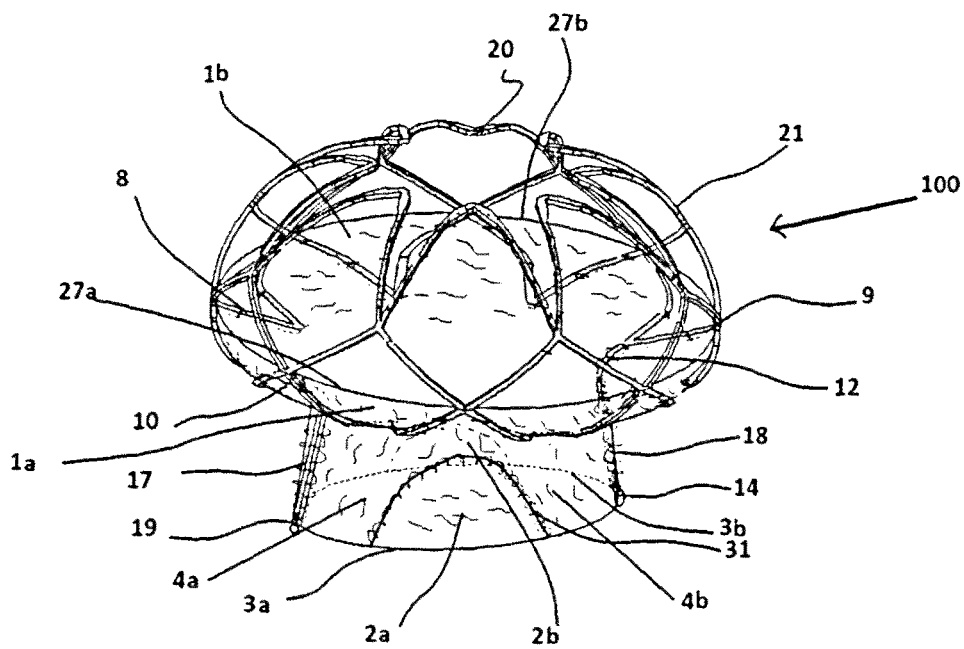
FIG. 1 is a perspective side view of a mitral valve assembly according to one embodiment of the present invention shown in an expanded configuration.
Figure 2:
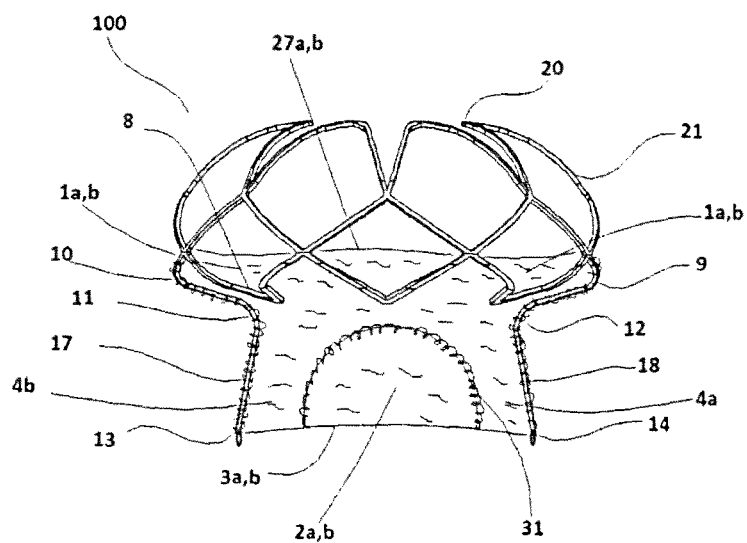
FIG. 2 is a side view of the assembly of FIG. 1.
Figure 3:
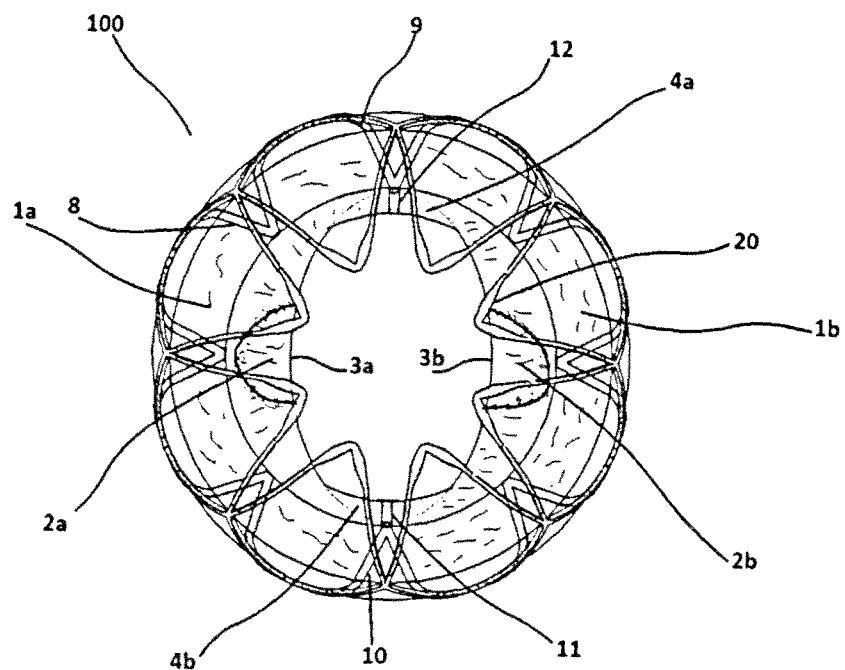
FIG. 3 is a top view of the assembly of FIG. 1.
Figure 4:
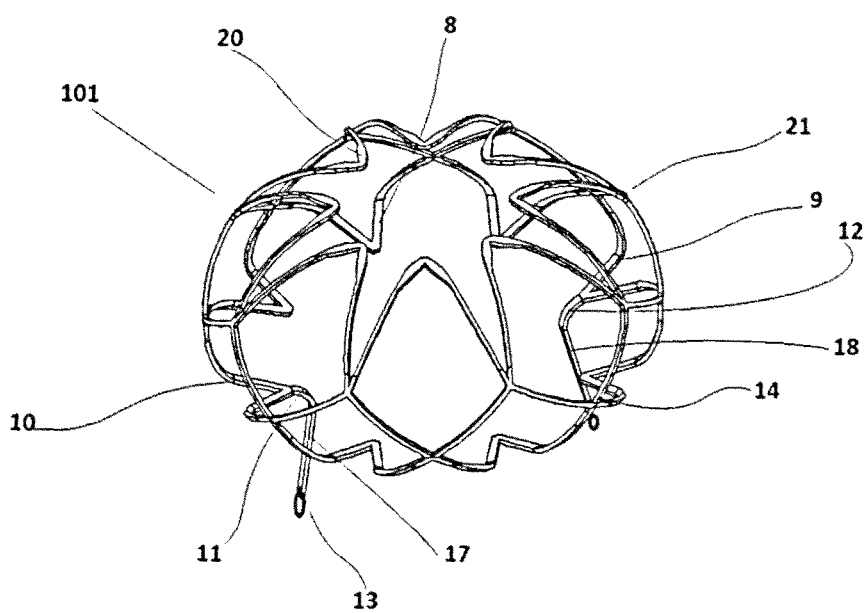
FIG. 4 is a perspective view of the frame of the assembly of FIG. 1.
Figure 5:
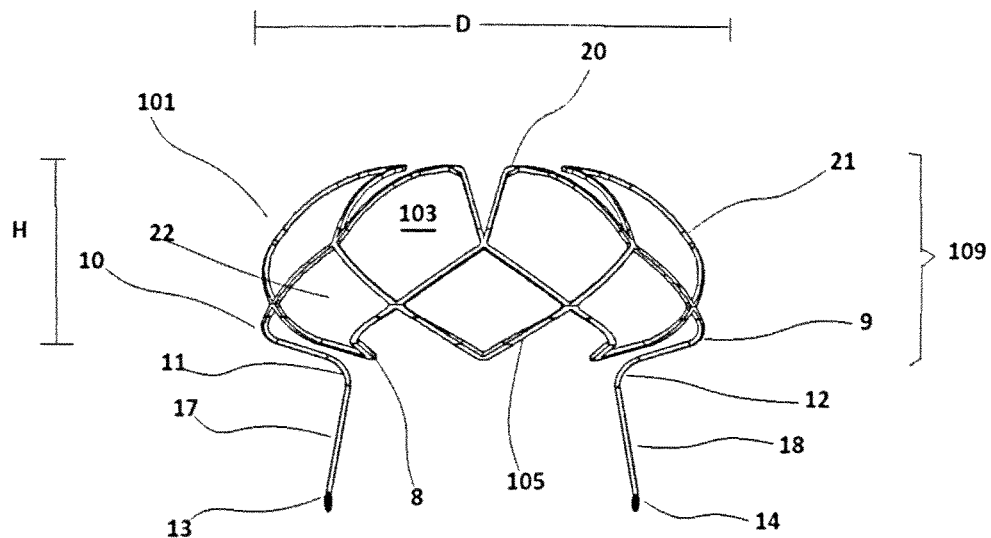
FIG. 5 is a side view of the frame of FIG. 4.

The following detailed description is of the best presently contemplated modes of carrying out the invention. This description is not to be taken in a limiting sense, but is made merely for the purpose of illustrating general principles of embodiments of the invention. The scope of the invention is best defined by the appended claims.

The present invention provides a mitral valve assembly 100 that is shown in fully assembled form in FIGS. 1-8. The assembly 100 has a frame 101 (see FIGS. 4-5) that has a simple leaflet valve support structure that can be effectively secured at the native mitral valve annulus. In addition, the leaflet assembly 104 (FIGS. 6-8) provides a novel leaflet configuration which provides fast opening and closing of the valve leaflets, with a large effective opening orifice area. The overall construction of the device 100 is simple, and effective in promoting proper mitral valve function.

As shown in FIGS. 1-5, the frame 101 has a ball-shaped anchoring section 109 that is adapted to be positioned inside the left atrium of a patient's heart. Two legs 17 and 18 extend from the downflow end of the anchoring section 109 through the native mitral annulus and into the left ventricle. The legs 17, 18 and the section 109 can be made of one continuous wire, and can be made from a thin wall biocompatible metallic element (such as stainless steel, Co—Cr based alloy, Nitinol™, Ta, and Ti etc.). As an example, the wire can be made from a Nitinol™ wire that is well-known in the art, and have a diameter of 0.2" to 0.4". The section 109 defines open cells 103 within the frame 101. Each cell 103 can be defined by a plurality of struts 105 that encircle the cell 103.

The anchoring section 109 functions to secure or anchor the assembly 100, and specifically the frame 101, inside the left atrium. The anchoring section 109 has a generally ball-shaped configuration defined by two annular rows of cells 103, with the cells 103 in the first row 21 having an apex 20 at the inflow end, and with the cells 103 in the second row 22 having an apex 8 at the outflow end. Each row of cells 103 has an annular zig-zag arrangement of struts that defines peaks and valleys. The term "ball-shaped" is intended to mean a generally spherical or oval-spherical shape that is similar to the shape of a native left atrium. Thus, the anchoring section 109 is shaped to have a somewhat spherical ball-like configuration when in its expanded or deployed configuration, with the apices 20 defining an annular opening at the inflow end, and with the apices 8 defining an annular opening at the outflow end. In addition, the shapes and sizes of the cells 103 can vary throughout the section 109. For example, the cells 103 are shown as being somewhat diamond-shaped, and the cells 103 in the row 21 can be generally larger than the cell 103 in the row 22.

Figure 9:
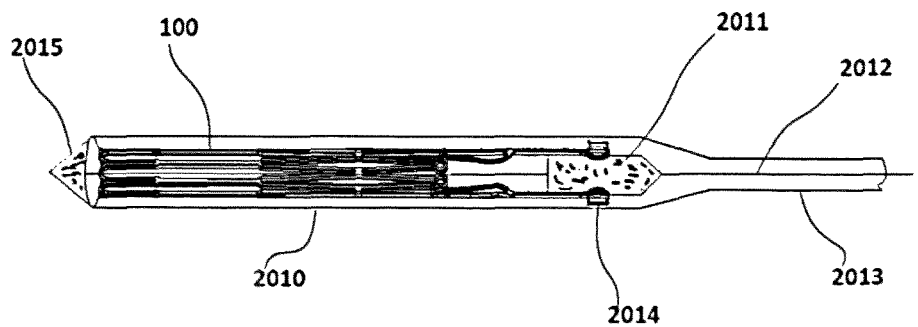
FIG. 9 illustrates a delivery system that can be used to deploy the assembly of FIG. 1.

The legs 17 and 18 extend from two opposite cells 103. Specifically, the leg 17 begins at a bend 10 that extends from one of the cells 103, transitions along a straight section to a second bend 11, and then extends vertically along another straight section to a tip or locking ear 13. Similarly, the leg 18 begins at a bend 9 that extends from an opposite cell 103, transitions along a straight section to a second bend 12, and then extends vertically along another straight section to a tip or locking ear 14. The legs 17 and 18 function to support and hold the leaflet sections 1a and 1b described below. As shown in FIG. 1, the leaflet sections 1a and 1b can be sewn directly to the legs 17 and 18. The locking ears 13 and 14 can be provided in various shapes such as rings, T-shaped, or square shaped, so as to match the ones in the ear hub 2014 of the delivery system as shown in FIG. 9. The locking ears 13 and 14 are used to secure the valve assembly 100 in the delivery system.

The following are some exemplary and non-limiting dimensions for the frame 101. For example, referring to FIG. 5, the height H of the anchoring section 109 can be between 15-40 mm; and the diameter D of the anchoring section 109 at its widest point can be between 20-50 mm.

In addition, the length of the legs 17 and 18 can vary depending on the number of leaflet sections 1a, 1b supported therein. For example, in the embodiment illustrated in FIGS. 1-8 where bi-leaflet sections 1a, 1b are provided, the length of the legs 17, 18 can be about 10-30 mm. If four leaflet sections 1a, 1b are provided, the length of the legs 17, 18 can be shorter, such as 10-20 mm. These exemplary dimensions can be used for an assembly 100 that is adapted for use at the native mitral position for a generic adult.

Figure 6:
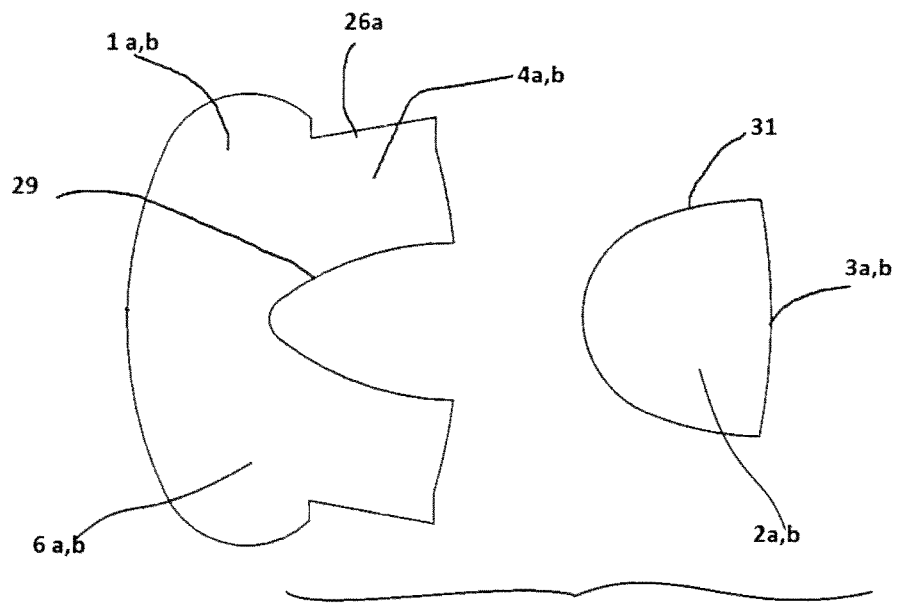
FIG. 6 is an exploded view of the leaflet assembly of the assembly of FIG. 1.
Figures 7A, 7B:
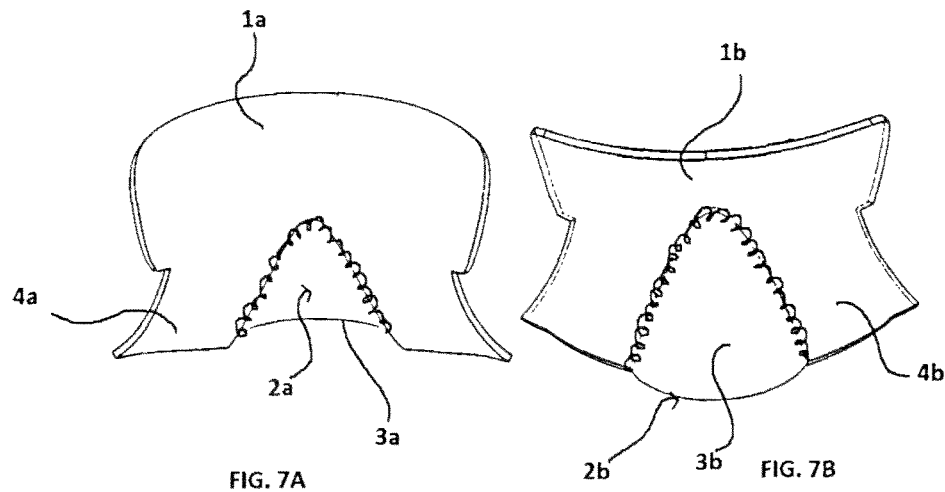
FIG. 7A is a front view of the leaflet assembly of FIG. 6.
FIG. 7B is a rear view of the leaflet assembly of FIG. 6.
Figure 8:
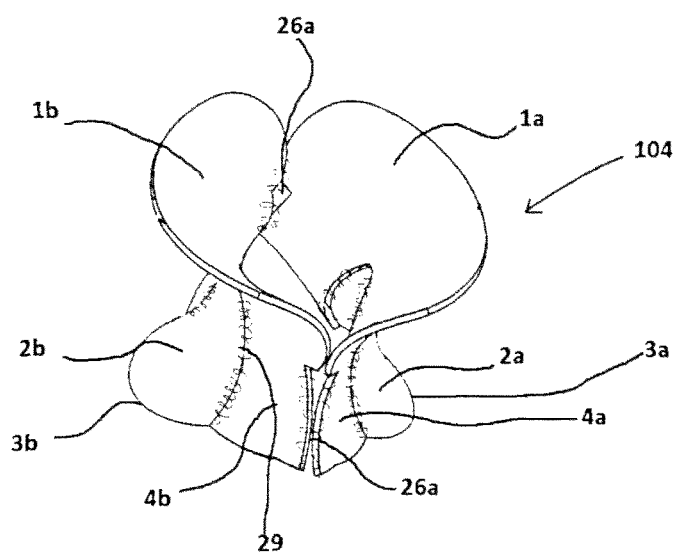
FIG. 8 is a perspective view of the leaflet assembly of FIG. 6.

Referring to FIGS. 6-8, the present invention provides a novel leaflet assembly 104 that provides a better coaptation between the leaflets. This leaflet assembly 104 can be the same as the leaflet assembly shown and described in Ser. No. 14/595,433, filed Jan. 13, 2015, whose entire disclosure is incorporated by this reference as though set forth fully herein.

The leaflet assembly 104 provides two separate leaflets, each of which is comprised of an upper skirt section 1a or 1b, and a lower sinus leaflet section 2a or 2b. In other words, sections 1a and 2a make up one leaflet, and sections 1b and 2b make up the other leaflet. As best shown in FIGS. 6, 7A and 7B, the skirt sections 1a and 1b are identical, and each has a larger-diameter semi-oval flange portion 6a or 6b, and a smaller-diameter body portion 4a or 4b. Each body portion 4a or 4b has opposing side edges 26a that function as commissure folding lines along which the side edges 26a may be stitched to assemble the two separate leaflets into a single leaflet assembly 104. Each body portion 4a or 4b also has a central U-shaped opening defined by stitching edge 29, which is adapted to receive the curved edge of the corresponding sinus leaflet section 2a or 2b. Each skirt section 1a, 1b creates an oval-shaped site on the top of the natural annulus.

Each sinus leaflet section 2a or 2b has a generally semi-circular shape, including an outflow edge 3a or 3b, and a curved edge defined by stitching edge 31. Each sinus leaflet section 2a or 2b is stitched along its stitching edge 31 to the stitching edge 29 of the corresponding body portion 4a or 4b.

The leaflet material can be a treated animal tissue such as pericardium, or from biocompatible polymer material (such as PTFE, Dacron, bovine, porcine, etc.). The leaflet sections 1a, 1b, 2a and 2b can also be provided with a drug or bioagent coating to improve performance, prevent thrombus formation, and promote endothelialization, and can also be treated (or be provided) with a surface layer/coating to prevent calcification.

The assembly 100 of the present invention can be compacted into a low profile and loaded onto a delivery system, and then delivered to the target location by a non-invasive medical procedure, such as through the use of a delivery catheter through transapical, or transfemoral, or transseptal procedures. The assembly 100 can be released from the delivery system once it reaches the target implant site, and can expand to its normal (expanded) profile either by inflation of a balloon (for a balloon expandable frame 101) or by elastic energy stored in the frame 101 (for a device where the frame 101 is made of a self-expandable material).

FIGS. 9-11B illustrate how the assembly 100 can be deployed at the pulmonary trunk of a patient's heart using a transapical delivery. Referring now to FIG. 9, the delivery system includes a delivery catheter having an outer shaft 2013, and an inner core 2012 extending through the lumen of the outer shaft 2013. An ear hub 2011 extends from the inner core 2012, and ear hub 2011 is also connected to a distal tip 2015. On the ear hub 2011, there are ears 2014 matching the locking ears 13, 14 (FIG. 1-5). A capsule 2010 is connected to and extends from the distal end of the outer shaft 2013 and is adapted to surround and encapsulate the assembly 100. A shaft extends from the legs 17 and 18 through the internal lumen of the assembly 100 to a distal tip 2015. The device 100 is crimped and loaded on the inner core 2012, and then compressed to the ears 2014 on ear hub 2011 with the locking ears 13, 14 (FIG. 1-5) locked in the ears 2014 (FIG. 9). The locked assembly 100 and ear hub 2011 are then covered by the capsule 2010.

Figure 10A:
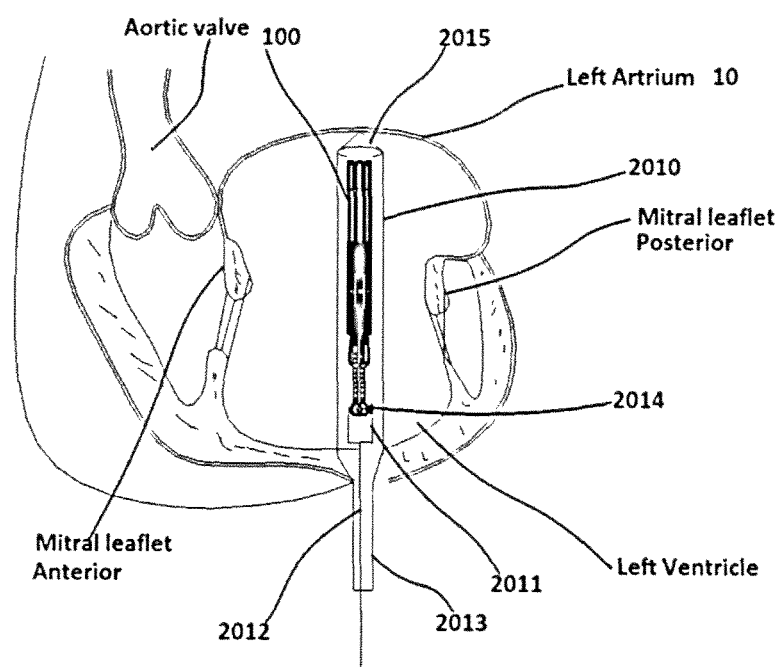
FIG. 10A illustrates transapical delivery of the assembly of FIG. 1 to the mitral position of a patient's heart.
Figure 10B:
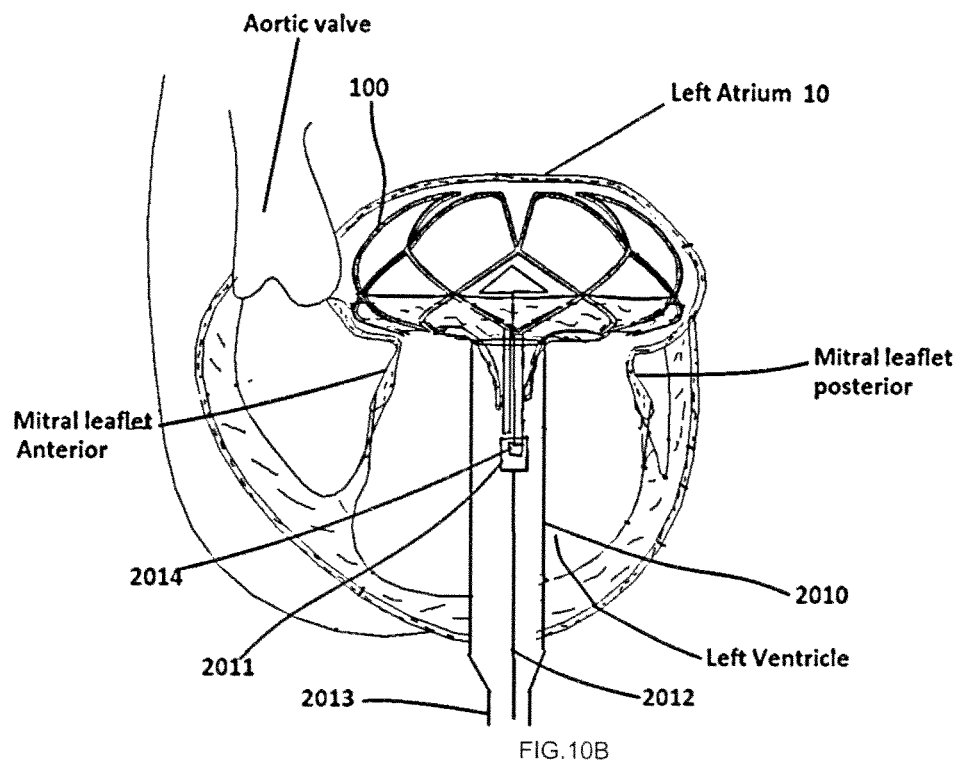
FIG. 10B illustrates partial deployment of the assembly of FIG. 1 in the mitral position of a patient's heart.

Referring now to FIG. 10A, the assembly 100 is shown in a collapsed configuration in the capsule 2010 and being delivered to the mitral position via a transapical delivery technique. In FIG. 10B, the capsule 2010 is partially withdrawn to partially expose the assembly 100 so that the self-expanding frame 101 will deploy the anchoring section 109 in the left atrium. As shown in FIG. 10B, the anchoring section 109 is shaped so that it conforms to the shape and configuration of a native left atrium, thereby allowing the anchoring section 109 to seat inside the left atrium in a manner such that the anchoring section 109 retains the entire assembly 100 in a somewhat fixed position without the need for using hooks, barbs or other tissue-piercing mechanisms.

Figure 11A:
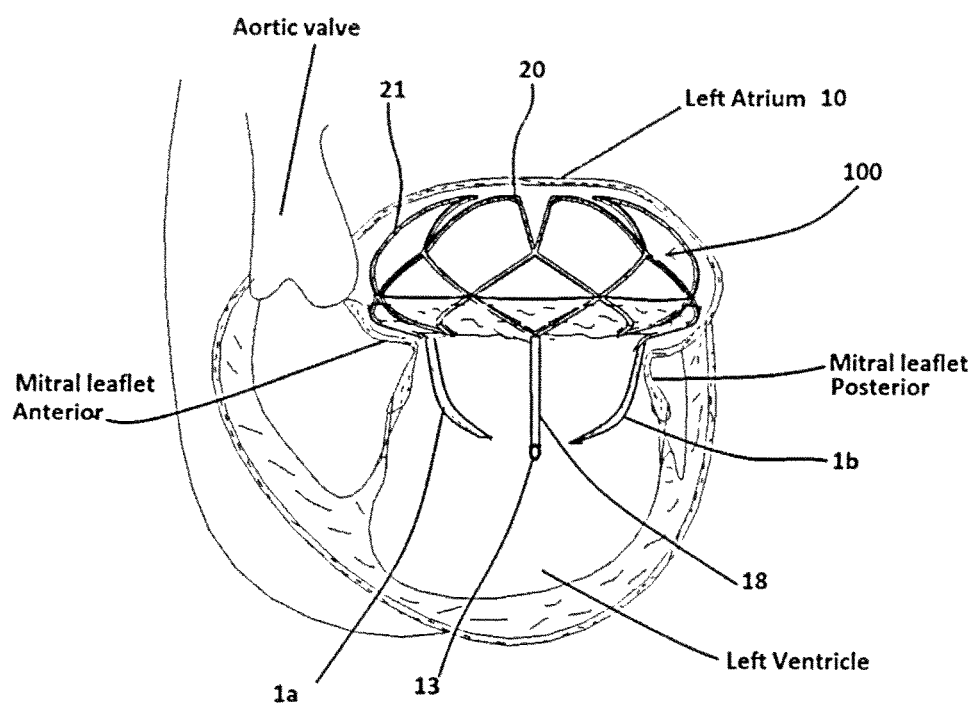
FIG. 11A illustrates the assembly of FIG. 1 in an open position in the mitral position of a human heart.
Figure 11B:
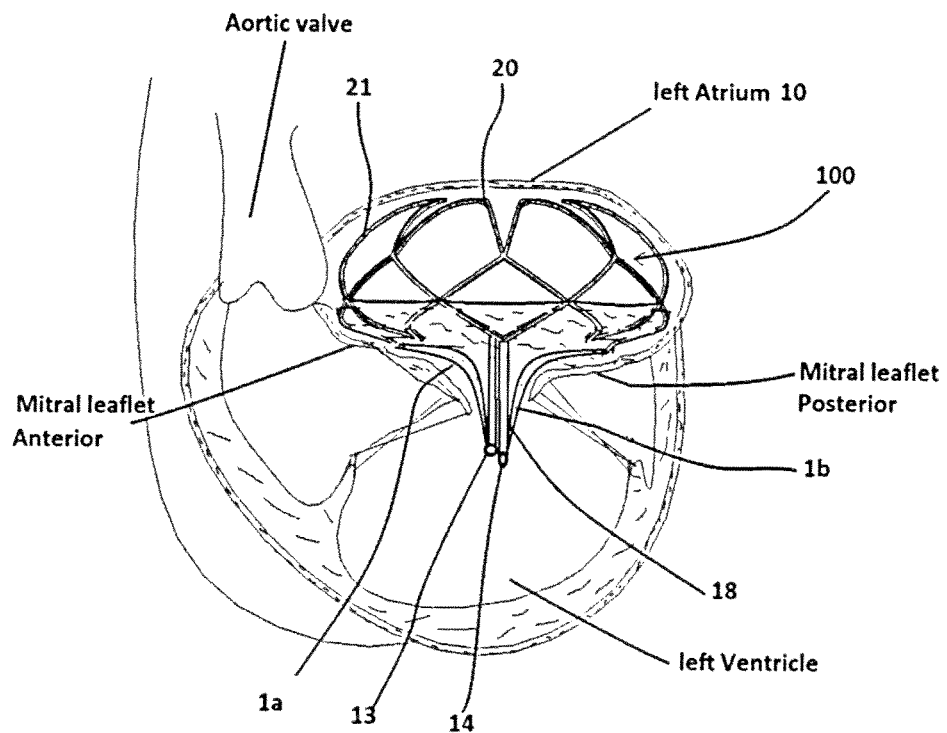
FIG. 11B illustrates the assembly of FIG. 1 in a closed position in the mitral position of a human heart.

When the capsule 2010 is completely withdrawn, as shown in FIGS. 11A and 11B, the legs 17 and 18 extend through the native annulus with the anchoring section 109 positioned entirely inside the left atrium. The leaflet sections 1a, 1b also extend through the native mitral annulus. FIG. 11A illustrates the leaflet assembly 100 in an opened position, and FIG. 11B illustrates the leaflet assembly 100 in a closed position. As shown in these drawings, the assembly 100 allows the native leaflets to function in a normal manner, with the leaflet sections 1a, 1b functioning to compensate for the defective function (e.g., mitral regurgitation—leaking mitral valve) of the native leaflets.

Thus, when the assembly 100 is deployed and aligned with the native mitral valve, the ball-shaped configuration of the anchoring section 109 allows most of the assembly 100 to be retained inside the left atrium 10, and with the leaflet sections 1a, 1b positioned securely within the mitral annulus at a position where they wedge into or push aside the native leaflets, without the use of any hooks or barbs or other similar securing mechanisms. The leaflet sections 1a, 1b, work to compensate for the native defective leaking mitral valves, thereby together function to create a "seal" to prevent leakage or back-flow blood flow back from the left ventricle to the left atrium).

The assembly 100 of the present invention provides a number of benefits. First, the manner in which the anchoring section 109 is retained inside the left atrium provides effective securement without the use of barbs or hooks or other invasive securement mechanisms. The securement is effective because it minimizes up and down migration of the assembly 100. Second, the configuration of the anchoring section 109 allows the assembly 100 to adapt to left atriums having different sizes and shapes, thereby reducing sizing and shaping problems by allowing each model or size of the assembly 100 to be used with a greater range of patients.

Third, this assembly 100 causes minimum alteration of the patient's anatomy by not expanding the annulus or affecting the aortic valve functions. The anchoring section 109 in the left ventricle has a simple structure without altering the native chordae or the valves, minimizing the impact on the blood fluid dynamics.

While the description above refers to particular embodiments of the present invention, it will be understood that many modifications may be made without departing from the spirit thereof. The accompanying claims are intended to cover such modifications as would fall within the true scope and spirit of the present invention.

What is claimed is:

1. A heart valve assembly, comprising:
   a frame comprising:
      a ball-shaped anchoring section defined by a plurality of rows of cells that includes a first row of cells and a second row of cells, with each cell defined by a plurality of struts that encircle each cell, with each row of cells having an annular zig-zag arrangement of struts that defines peaks and valleys, and wherein the zig-zags of the cells in the first row define a first apex which defines a first opening at an inflow end, and the zig-zags of the cells in the second row define a second apex which defines a second opening at an outflow end, with a longitudinal axis extending through the first and second openings;
      exactly two legs extending from two opposite cells of the second row of cells of the anchoring section, with each of the two legs beginning at a first bend that extends from one of the two opposite cells, and then transitioning along a first straight section that extends towards the longitudinal axis to a second bend, and then extending vertically along a second straight section to a tip; and
   a leaflet assembly having a plurality of leaflets that are stitched to the two legs.

2. The assembly of claim 1, wherein each tip comprises an ear.

3. The assembly of claim 2, wherein each ear is ring-shaped, T-shaped, or square shaped.

4. The assembly of claim 1, wherein the anchoring section and the legs are all provided in a single piece.

5. The assembly of claim 1, wherein each cell is somewhat diamond-shaped.

6. The assembly of claim 1, wherein the plurality of leaflets consists of exactly two leaflets.

7. The assembly of claim 1, wherein the plurality of rows of cells consists of exactly two rows of cells.

* * * * *